(12) United States Patent
Navab et al.

(10) Patent No.: US 11,367,226 B2
(45) Date of Patent: Jun. 21, 2022

(54) CALIBRATION TECHNIQUES FOR ALIGNING REAL-WORLD OBJECTS TO VIRTUAL OBJECTS IN AN AUGMENTED REALITY ENVIRONMENT

(71) Applicant: THE JOHNS HOPKINS UNIVERSITY, Baltimore, MD (US)

(72) Inventors: Nassir Navab, Baltimore, MD (US); Javad Fotouhi, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 17/182,636

(22) Filed: Feb. 23, 2021

(65) Prior Publication Data

US 2021/0272328 A1  Sep. 2, 2021

Related U.S. Application Data

(60) Provisional application No. 62/983,359, filed on Feb. 28, 2020.

(51) Int. Cl.
*G06T 11/00* (2006.01)
*G09G 5/38* (2006.01)
*G02B 27/01* (2006.01)
*A61B 90/50* (2016.01)
*A61B 90/00* (2016.01)

(52) U.S. Cl.
CPC ............. *G06T 11/00* (2013.01); *A61B 90/50* (2016.02); *G02B 27/0172* (2013.01); *G09G 5/38* (2013.01); *A61B 2090/365* (2016.02); *A61B 2090/502* (2016.02); *G09G 2340/12* (2013.01); *G09G 2380/08* (2013.01)

(58) Field of Classification Search
None
See application file for complete search history.

(56) References Cited

U.S. PATENT DOCUMENTS

| | | | |
|---|---|---|---|
| 10,510,137 B1* | 12/2019 | Kitain | G02B 27/0093 |
| 2015/0062120 A1* | 3/2015 | Reisner-Kollmann | G06T 19/006 345/419 |
| 2018/0205933 A1* | 7/2018 | Aflaki Beni | G02B 27/017 |
| 2019/0056693 A1* | 2/2019 | Gelman | G02B 27/017 |
| 2020/0129136 A1* | 4/2020 | Harding | A61B 6/44 |
| 2020/0265598 A1* | 8/2020 | Iyer | G06T 7/579 |

\* cited by examiner

*Primary Examiner* — Jwalant Amin
(74) *Attorney, Agent, or Firm* — MH2 Technology Law Group LLP

(57) ABSTRACT

A method for aligning a real-world object with a virtual object includes capturing images, video, or both of the real-world object from a first viewpoint and from a second viewpoint. The first and second viewpoints are different. The method also includes simultaneously superimposing the virtual object at least partially over the real-world object from the first viewpoint in a first augmented reality (AR) display and from the second viewpoint in a second AR display based at least in part on the images, video, or both. The method also includes adjusting a position of the real-world object to at least partially align the real-world object with the virtual object from the first viewpoint in the first AR display and from the second viewpoint in the second AR display.

19 Claims, 12 Drawing Sheets

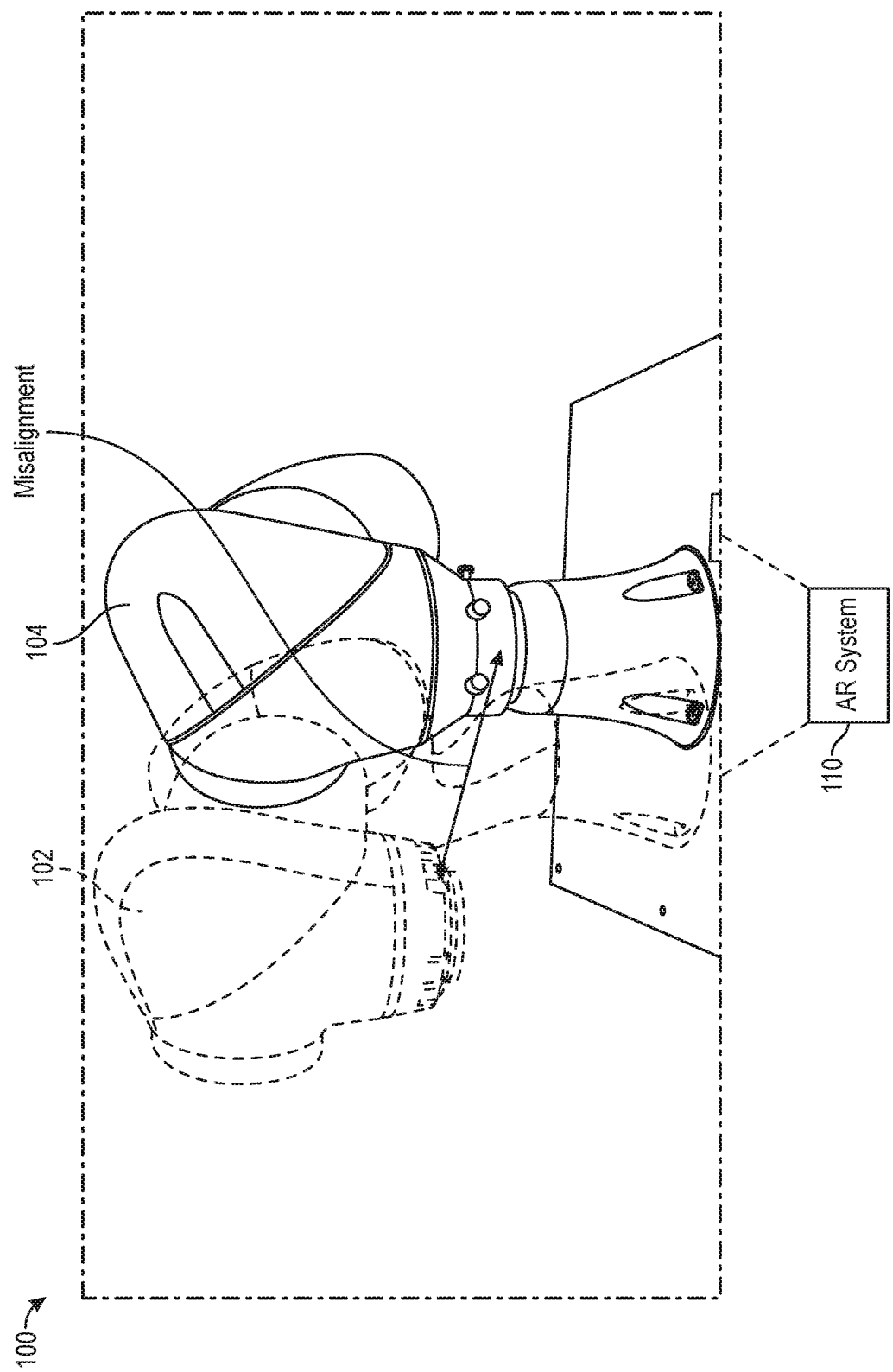

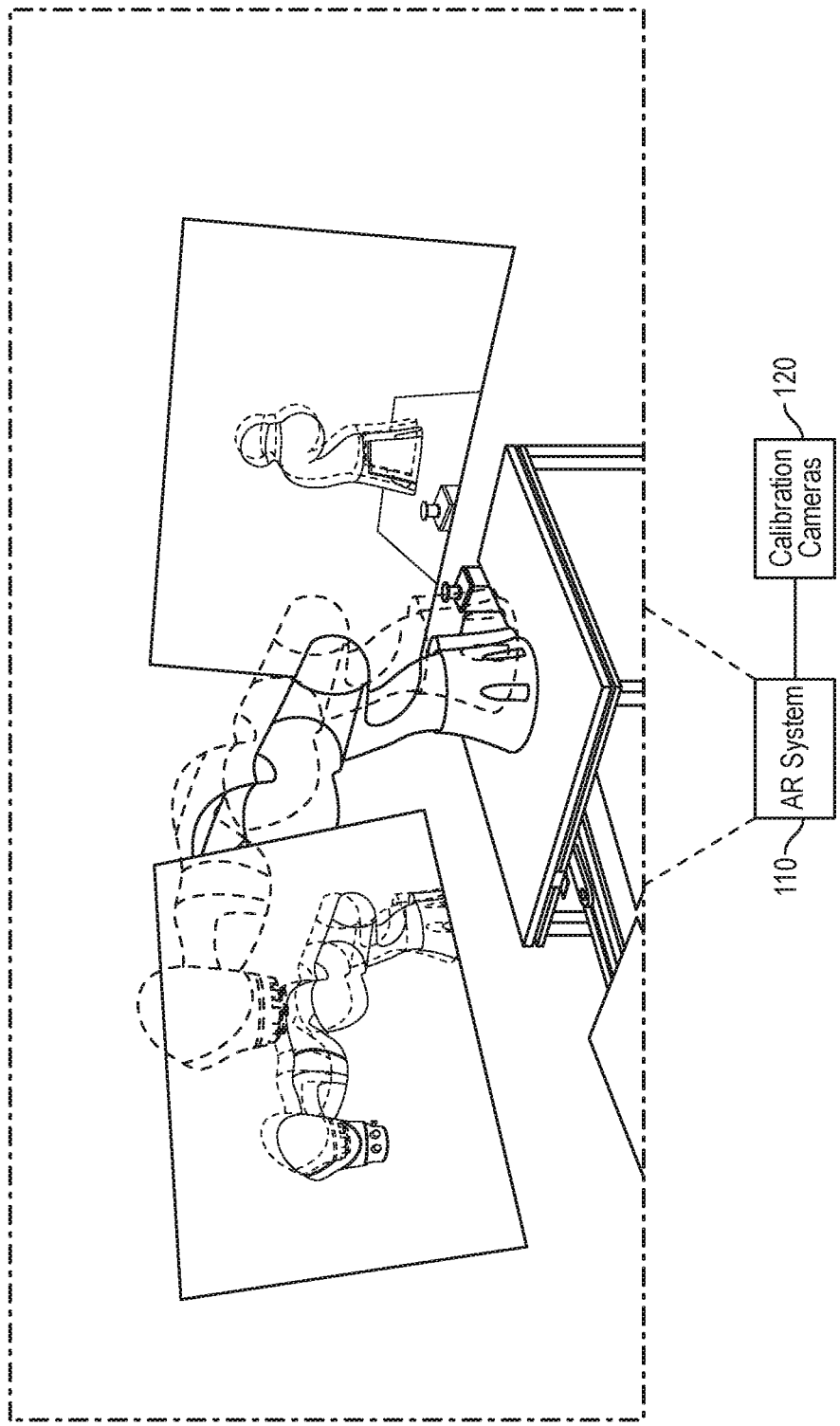

CALIBRATION TECHNIQUES FOR ALIGNING REAL-WORLD OBJECTS TO VIRTUAL OBJECTS IN AN AUGMENTED REALITY ENVIRONMENT

CROSS-REFERENCE TO RELATED APPLICATIONS

This application claims priority to U.S. Provisional Patent Application No. 62/983,359, filed on Feb. 28, 2020, the entirety of which is incorporated by reference herein.

BACKGROUND

A head-mounted display (HMD) is a display device, worn on the head or as part of a helmet, that includes a small display optic in front of one eye (monocular HMD) or each eye (binocular HMD). An HMD may be incorporated as part of an Augmented Reality (AR) or Virtual Reality (VR) system and may be used in a variety of applications, such as gaming, aviation, engineering, surgery/medicine, dentistry, etc. An optical head-mounted display (OHMD) is another type of wearable display that reflects projected images and allows a user to see through the reflected images.

SUMMARY

A method for aligning a real-world object with a virtual object is disclosed. The method includes capturing images, video, or both of the real-world object from a first viewpoint and from a second viewpoint. The first and second viewpoints are different. The method also includes simultaneously superimposing the virtual object at least partially over the real-world object from the first viewpoint in a first augmented reality (AR) display and from the second viewpoint in a second AR display based at least in part on the images, video, or both. The method also includes adjusting a position of the real-world object to at least partially align the real-world object with the virtual object from the first viewpoint in the first AR display and from the second viewpoint in the second AR display.

In another embodiment, the method includes capturing a first set of images, video, or both of the real-world object from a first viewpoint and from a second viewpoint. The first set is captured at a first time. The first and second viewpoints are different. The method also includes generating the virtual object based at least in part on the first set. The method also includes capturing a second set of images, video, or both of the real-world object from the first viewpoint and from the second viewpoint at a second time. The second time is after the first time. The method also includes displaying the real-world object from the first viewpoint in a first augmented reality (AR) display and from the second viewpoint in a second AR display based at least in part on the second set. The method also includes superimposing the virtual object at least partially over the real-world object from the first viewpoint in the first AR display and from the second viewpoint in the second AR display based at least in part on the first set and the second set. The method also includes adjusting a position of the real-world object to at least partially align the real-world object with the virtual object from the first viewpoint in the first AR display and from the second viewpoint in the second AR display.

A system for aligning a real-world object with a virtual object is also disclosed. The system includes a first camera configured to capture a first set of images, video, or both of the real-world object at a first time and a second set of images, video, or both of the real-world object at a second time. The first time is before the second time. The first and second sets are from a first viewpoint. The system also includes a second camera configured to capture a third set of images, video, or both of the real-world object at the first time and a fourth set of images, video, or both of the real-world object at the second time. The third and fourth sets are from a second viewpoint. The first and second viewpoints are different. The system also includes a viewing device configured to display the virtual object from the first viewpoint in a first augmented reality (AR) display and from the second viewpoint in a second AR display based at least in part on the first set and the third set. The viewing device is also configured to display the real-world object from the first viewpoint in the first AR display and from the second viewpoint in the second AR display based at least in part on the second set and the fourth set. The system also includes a computing system configured to receive a user input in response to the virtual object and the real-world object in the first and second AR displays and to adjust a position of the real-world object to at least partially align the real-world object with the virtual object from the first viewpoint in the first AR display and from the second viewpoint in the second AR display.

BRIEF DESCRIPTION OF THE DRAWINGS

FIGS. 1A-1F illustrate an overview of an example a virtual object that is misaligned at various angles during a calibration procedure in accordance with aspects of the present disclosure.

FIGS. 2A-2C illustrate an example calibration environment and calibration process in accordance with aspects of the present disclosure.

DETAILED DESCRIPTION

Figure 1A:
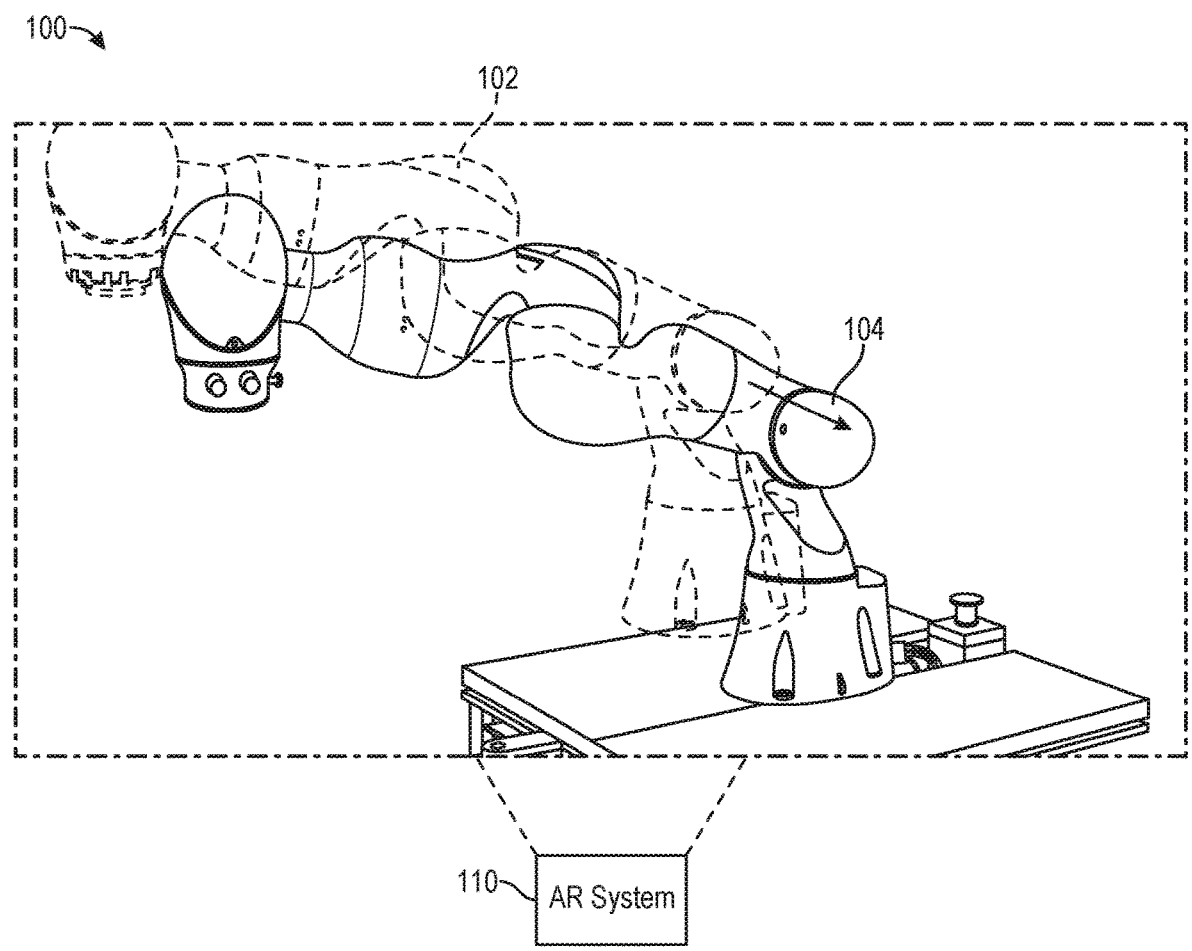
Figure 1B:
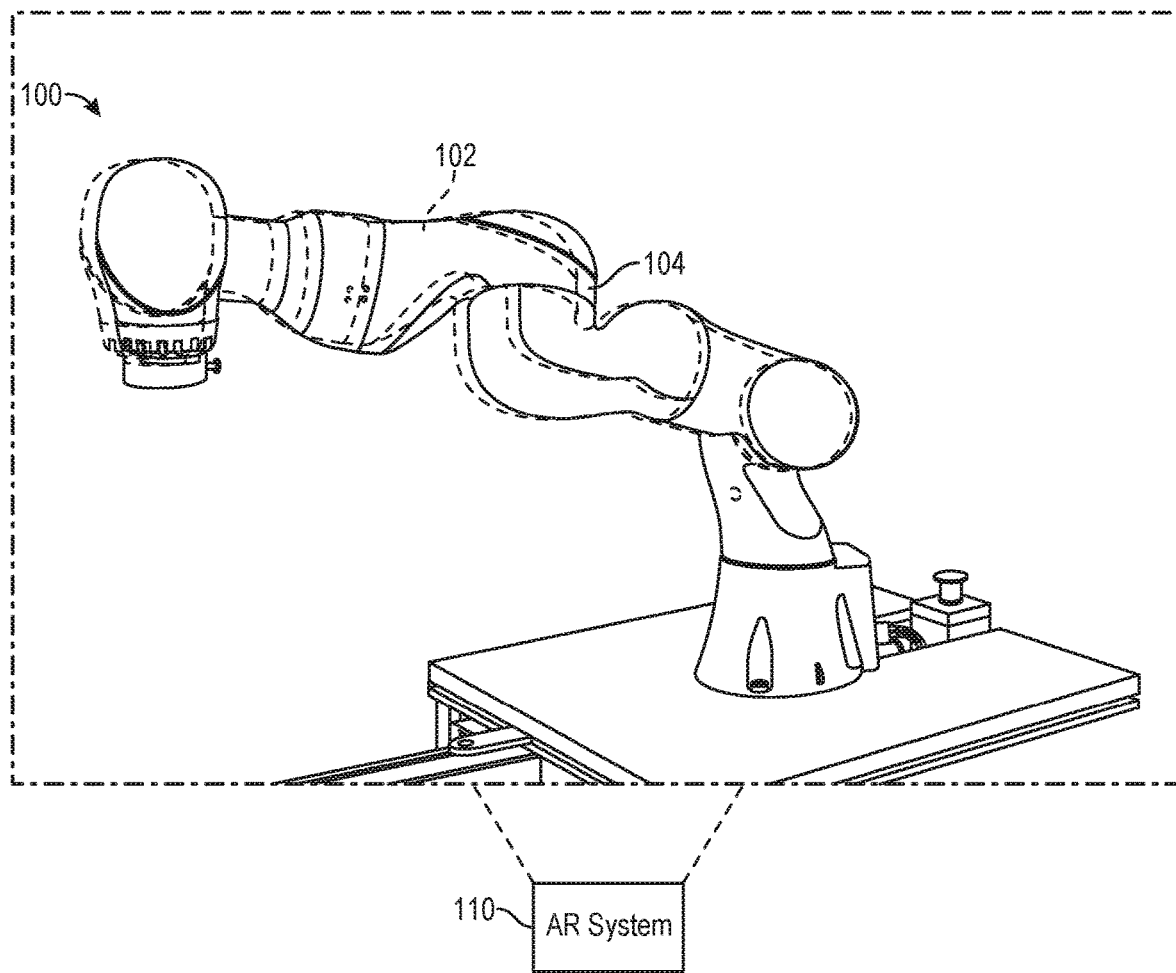
Figure 1C:
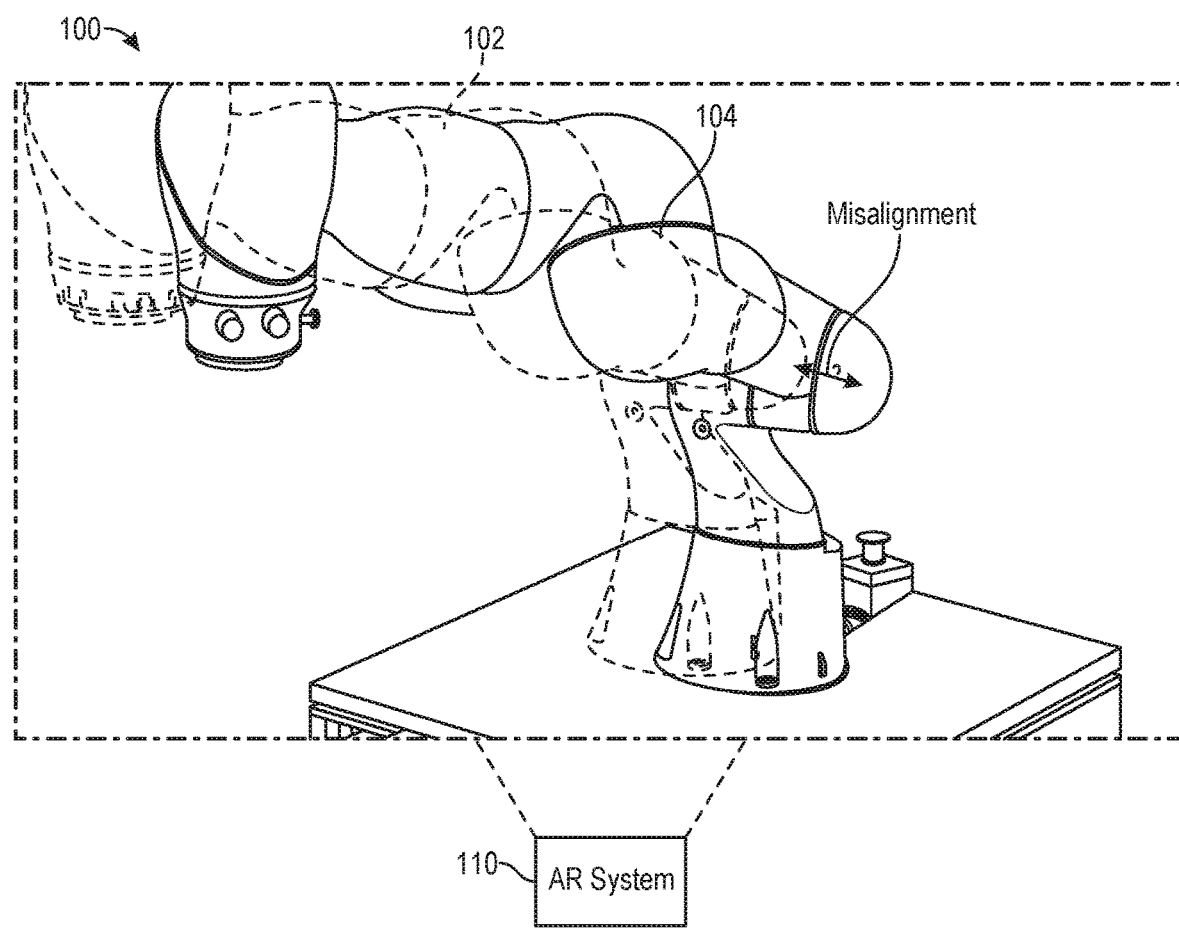
Figure 1D:
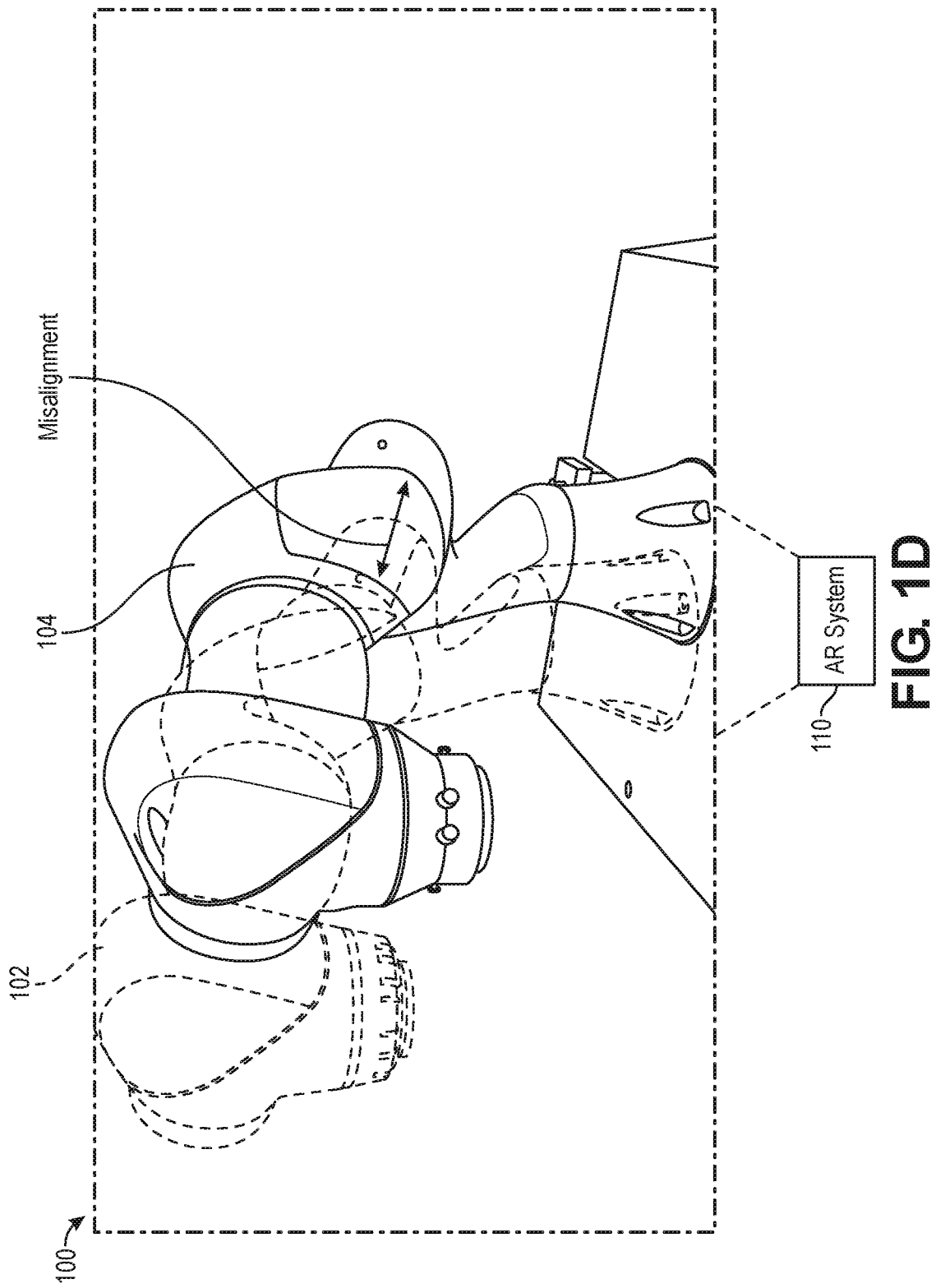
Figure 1E:
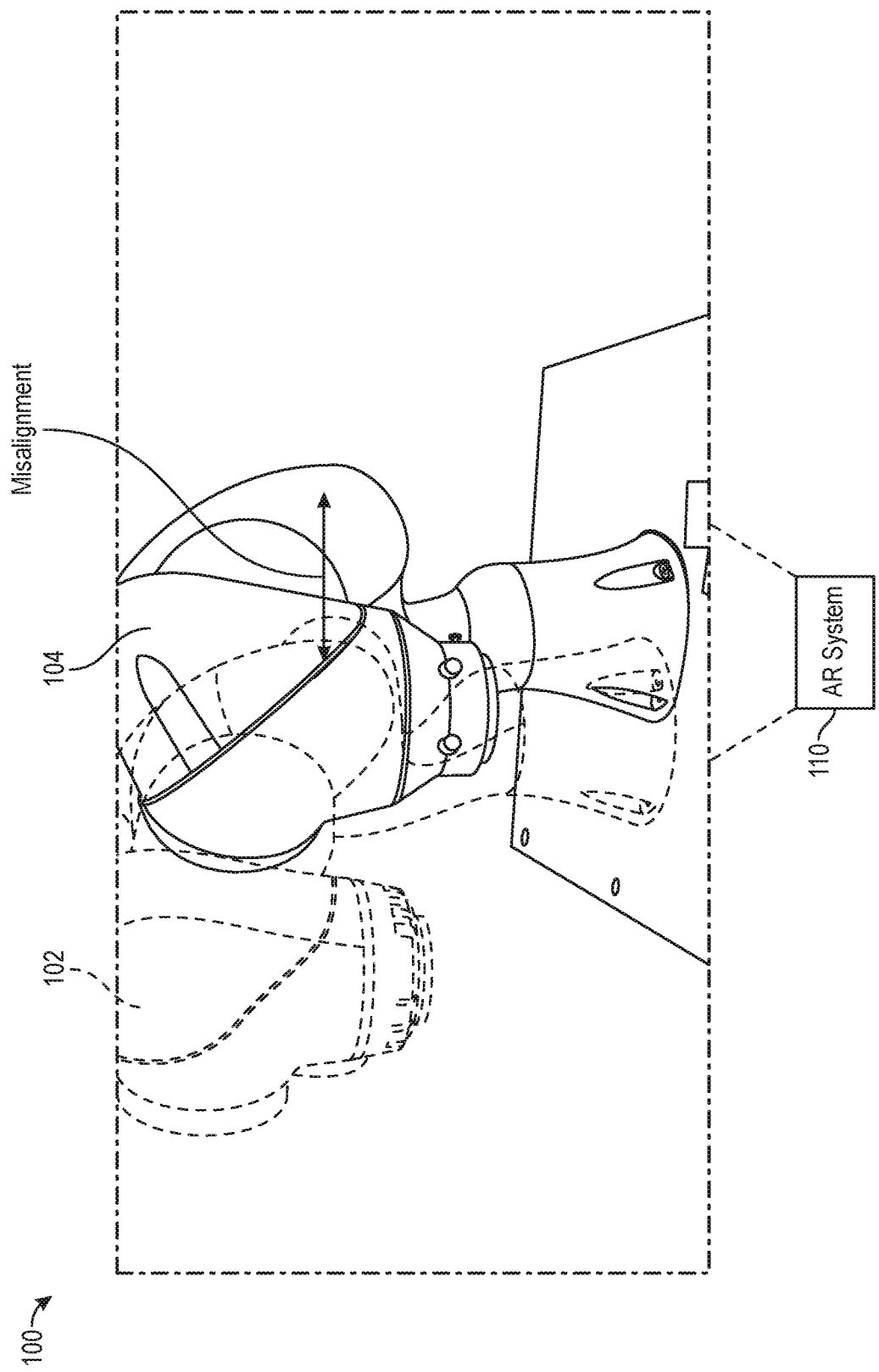

Aspects of the present disclosure may include a system and/or method to align a real-world object using a virtual image of the object in which the virtual image is presented through a display of an AR system (e.g., an HMD) and superimposed over real-world imagery. As one illustrative example, a virtual image of an object (e.g., a surgical arm) may be presented through an HMD and superimposed at an optimal position where a real-world surgical arm should be placed and aligned. As such, a user may view the optimal or correct placement, position, and alignment of the virtual surgical arm through an AR system, and place/position a real-world surgical arm in the corresponding position as shown through the AR system. Once properly position and aligned, the surgical arm may be used as part of a procedure (e.g., a surgical procedure).

Aspects of the present disclosure may further include a system and/or method to properly calibrate the alignment of virtual object rendering such that the virtual object is properly presented (e.g., without misalignments) through a display of an AR system based on the user's current viewing position, and/or current field of view. More specifically, aspects of the present disclosure may present a multi-view/multi-angle calibration environment in which a user may simultaneously view the rendering of a virtual object from multiple angles and fields of views. From the simultaneous views and angles, the user may provide user input to align the virtual object to a real-world object as part of a calibration process in which the positions of the virtual object with respect to different viewing angles are defined. The calibration definitions may be saved and used in runtime to render the virtual object with consideration to real-time viewing angles (e.g., the user's real-time or current field of view/viewing position). That is, in a runtime setting, the user's current field of view through an AR system may be monitored, and the rendering of the virtual object may be positioned with consideration to the user's current viewing position or field of view. In this way, the virtual object is properly rendered and presented when the virtual object is viewed through an AR system at different angles and positions.

As one illustrative, non-limiting example, a virtual surgical arm (viewable through an AR system) may be aligned with a real-world surgical arm at multiple viewing angles as part of a calibration definition process. In runtime, the calibration definitions may be used to present/render the virtual surgical arm based on the current viewing angle detected by the AR system, such that the virtual surgical arm is presented without misalignments. That is to say, without the calibration techniques described herein, the presentation of a virtual object would not be aligned and thus, in a runtime setting, the presentation of the virtual object would not correctly aid the user in placing and positioning the virtual object correctly.

While the systems and/or methods, described herein, describe the calibration and alignment of a real-world surgical arm to the projected position of a virtual surgical arm, the systems and/or methods are not so limited to this example. In practice, the systems, methods, and calibration techniques, described herein, may be used to align any variety of real-world objects to any corresponding variety of virtual objects. That is, the systems and/or methods described herein are not limited to surgical or medical applications. For example, the systems and/or methods described herein may be applied for architectural applications, design applications, manufacturing applications, etc.

Certain embodiments of the disclosure will hereafter be described with reference to the accompanying drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

Embodiments of the disclosure may include a system, a method, and/or a computer program product at any possible technical detail level of integration. The computer program product may include a computer readable storage medium (or media) having computer readable program instructions thereon for causing a processor to carry out aspects of the present disclosure.

FIGS. 1A-1F illustrate an overview of an example a virtual object that is misaligned at various angles during a calibration procedure. More specifically, FIGS. 1A-1F illustrate a situation in which the presentation of a virtual object is correctly aligned at one angle, but misaligned at other angles. As described herein, the systems and/or methods described herein include a calibration procedure to correct misalignments at various angles and generate calibration definitions which may then be used in runtime to present/render a virtual object with proper alignment when the virtual object is viewed at different angles and positions.

Referring to FIG. 1A, an AR system 110 may present an interface 100 through which virtual content may be presented over real-world imagery (e.g., as seen by the user when wearing the AR system 110). In the example of FIGS. 1A-1F, a virtual object 102 may be displayed and a real-world object 104 may be viewable within the interface 100. More specifically, the virtual object 102 may be a virtual, computer-generated, or digital rendering of the real-world object 104. As an illustrative, non-limiting example, the real-world object 104 may be a surgical arm, and the virtual object 102 may be a virtual, computer-generated, or digital rendering of the surgical arm.

As further shown in FIG. 1A, the rendering of the virtual object 102 may be moved (e.g., via user input) to align with the real-world object 104 (e.g., in the direction of the arrow as shown). For example, referring to FIG. 1B, the virtual object 102 is properly aligned with the real-world object 104. However, while the virtual object 102 may now be aligned with the real-world object 104 at the particular angle shown, the virtual object 102 may be misaligned with the real-world object 104 when viewed at different angles. For example, referring to FIGS. 1C-1F, it can be seen that a misalignment is present between the virtual object 102 and the real-world object 104 as the user's viewing angle changes. Accordingly, aspects of the present disclosure may include a calibration technique to present multiple views and angles during a calibration process for simultaneously aligning the virtual object 102. An example of the calibration technique and calibration environment is illustrated in FIGS. 2A-2C.

In some embodiments, a calibration environment may include multiple calibration cameras positioned around the virtual object 102 (and/or the real-world object 104) at different angles (e.g., to provide different viewing angles for calibration) in which the virtual object 102 may be a point of reference for which to align the real-world object 104. The calibration environment may include multiple calibration cameras 120 positioned around the virtual object 102 at different angles (e.g., to provide different viewing angles and points of view for calibration. The calibration environment may include any variety of and number cameras, camera mounts, hardware, tripods, etc. As an example, the calibration environment may include two calibration cameras, although in practice, additional or fewer calibration cameras may be used, and the techniques described herein are not limited to the number of calibration cameras used.

Figure 2A:
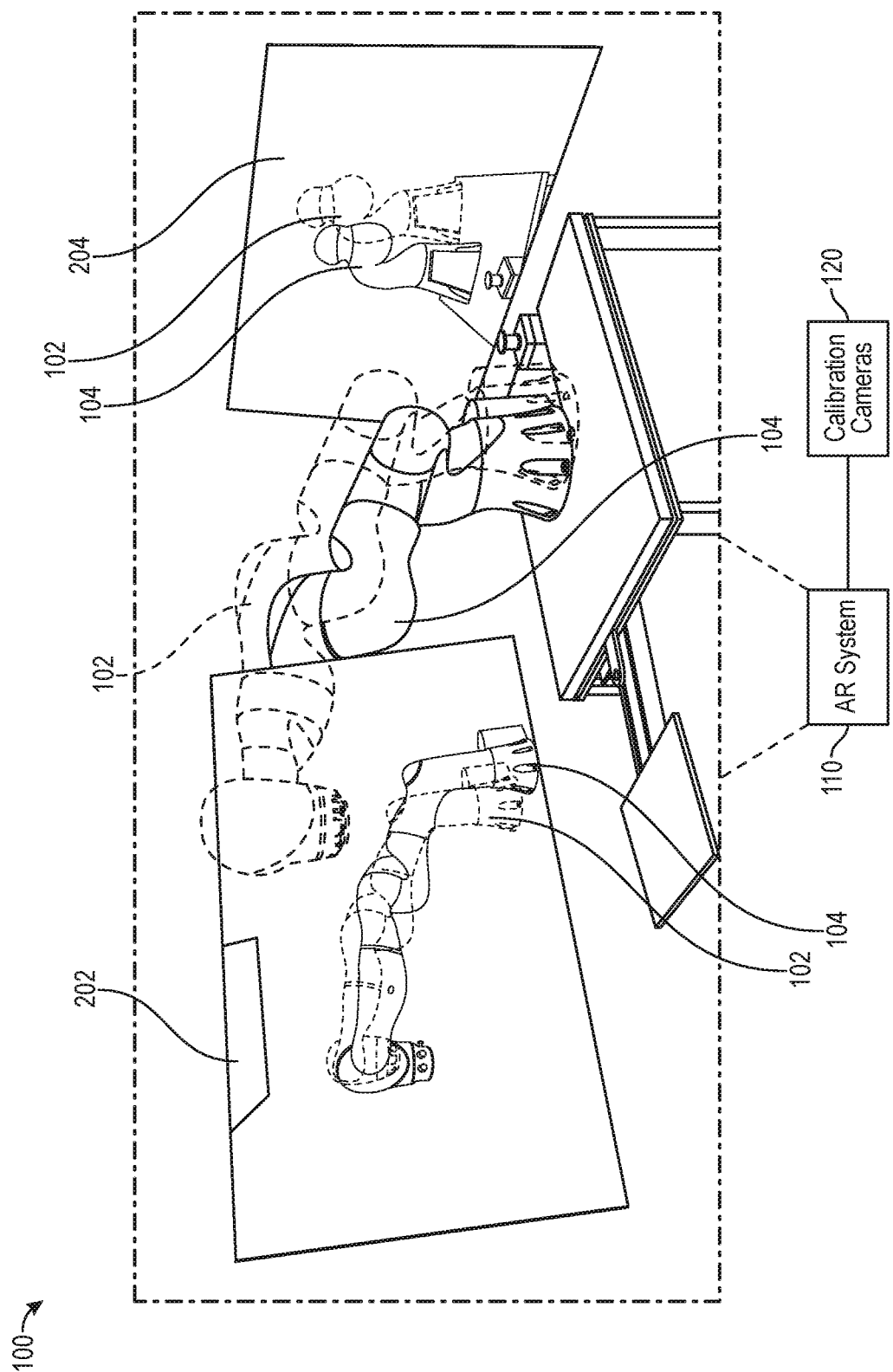
Figure 2C:
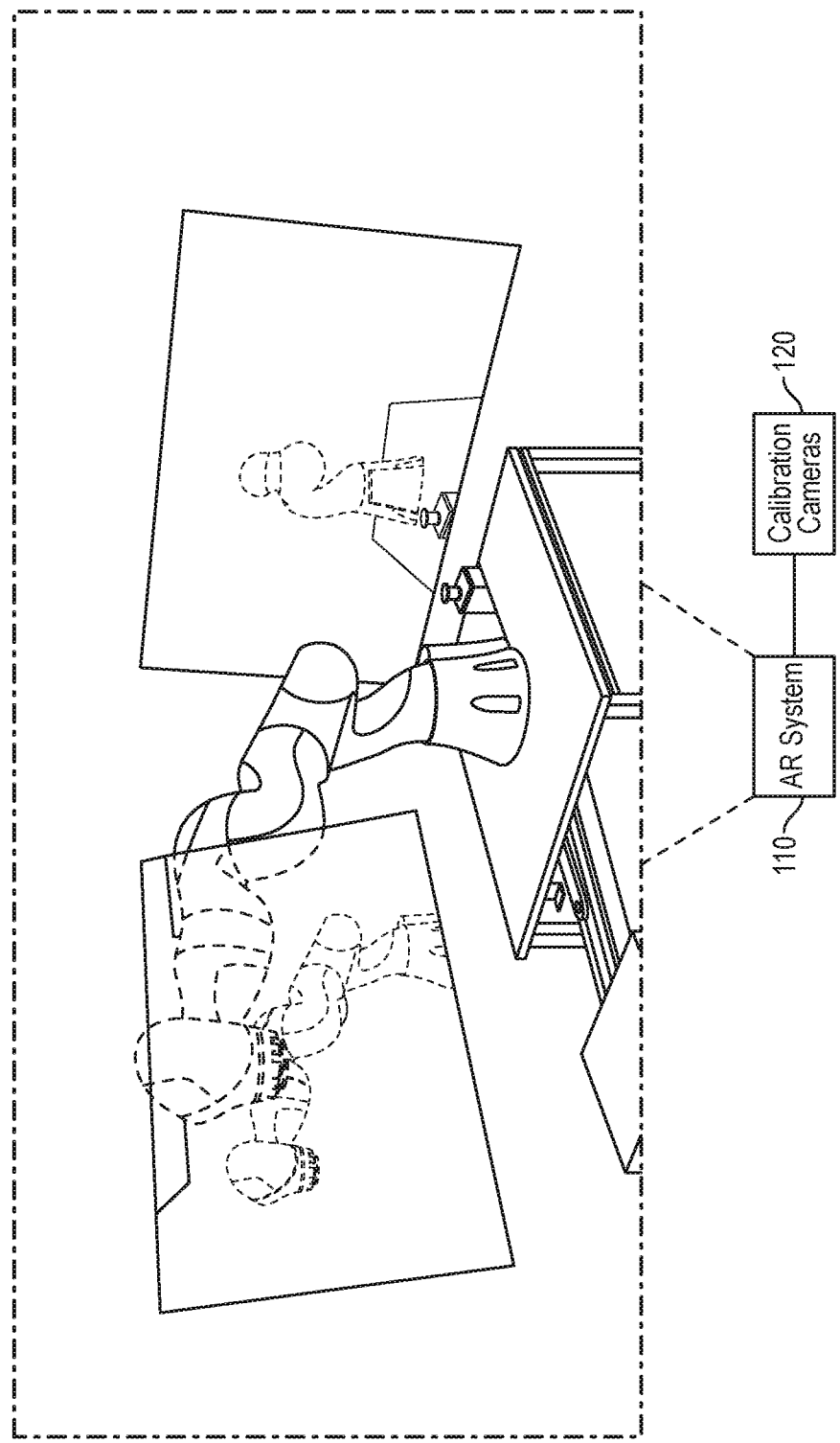

Referring to FIG. 2A, multiple views of the virtual object 102 and the real-world object 104 may be shown. For example, the interface 100 may include viewers 202 and 204. The viewers 202 and 204 may be reflective displays viewable within the interface 100 that present pictures and/or video captured by multiple calibration cameras 120 placed at different angles as part of a calibration process.

Thus, three instances of each of the virtual object 102 and the real-world object 104 are viewable from the interface 100 at different angles (e.g., one instance through viewer 202, one instance through viewer 204, and one instance as seen through the user's eyes).

At each instance in which the virtual object 102 and real-world object 104 can be seen, the user may provide user input to move and/or adjust the positioning of the virtual object 102 so as to align the virtual object 102 with the real-world object 104. That is, the real-world object 104 may serve as a point of reference with which to align the virtual object 102. This may calibrate the virtual object 102. In some embodiments, the user may provide user input (for aligning the virtual object 102 with the real-world object 104) through any variety or combination of suitable input techniques, such as hand gestures, voice commands, retina tracking, keypad, mouse input (e.g., virtual mouse, drag and drop input), etc. In one example, the user may provide input to individually align the virtual object 102 with the real-world object 104 at each angle, or the user input may be used to simultaneously align the virtual object 102 with the real-world object 104 at each angle. For example, referring to FIGS. 2B and 2C, the user may continue to provide user input as needed until the virtual object 102 is aligned with the real-world object 104 at each angle. Once alignment is complete, the AR system 110 may generate and save calibration definitions that identify the alignment coordinates in a coordinate system. That is to say, the user inputs that align the virtual object 102 with the real-world object 104 at each angle may define coordinates in a coordinate system indicating the locations in the coordinate system where the virtual object 102 should be presented based on the user's viewing angle. In general, the calibration definitions identify these coordinates indicating the locations where the virtual object 102 should be presented based on the user's viewing angle such that virtual object 102 is presented without misalignments.

In the examples shown in FIGS. 2A-2C, three angles may be used as part of the calibration process. However, additional calibration cameras 120 may be provided and used so that additional angles may be used in the calibration process. Further, even though the user may align the virtual object 102 with the real-world object 104 at a few different angles, the AR system 110 may interpolate calibration definitions at other angles using any variety or combination of interpolation techniques.

Figure 3:
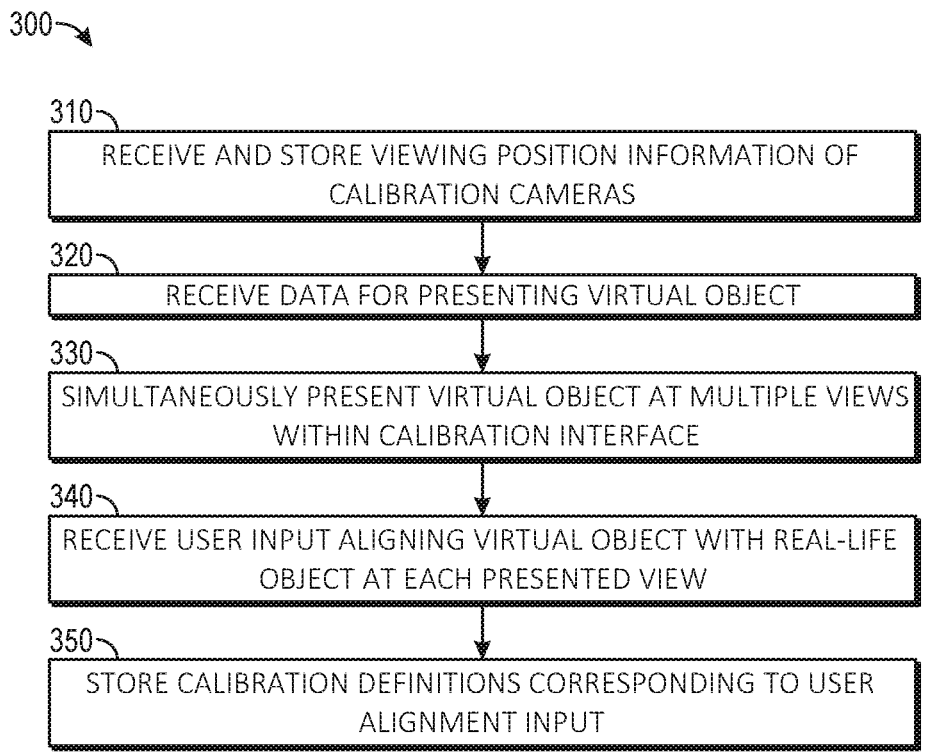
FIG. 3 illustrates an example flowchart of a process for a calibrating the alignment of a virtual object at multiple angles in accordance with aspects of the present disclosure.

FIG. 3 illustrates an example flowchart of a process for calibrating the alignment of a virtual object at multiple angles in accordance with aspects of the present disclosure. The blocks of FIG. 3 may be implemented within a calibration environment, (e.g., the calibration environment). The flowchart of FIG. 3 illustrates the architecture, functionality, and operation of possible implementations of systems, methods, and computer program products according to various embodiments of the present disclosure.

As shown in FIG. 3, process 300 may include receiving and storing viewing position information of calibration cameras (block 310). For example, the AR system 110 may receive and store information identifying the viewing positions of the calibration cameras 120 in the calibration environment. As used herein, the "viewing position" may refer to three-dimensional spatial information, angles, heights, depths, etc. More specifically, the AR system 110 may receive information identifying the viewing angle and/or three-dimensional spatial coordinates representing the position, location, angle, etc. of each of the calibration cameras 120. In some embodiments, the viewing positions of the calibration cameras 120 may be coordinates in a coordinate system.

Process 300 also may include receiving data for presenting the virtual object (block 320). For example, the AR system 110 may receive the data or parameters of the virtual object to be presented (e.g., data that identifies the size, shape, model, type, color, dimensions, perimeter, borders/boundaries, etc. relating to the object's appearance). As an illustrative example, the AR system 110 may receive a data file representing a virtual surgical arm that the AR system 110 may use to present the virtual surgical arm.

Process 300 further may include simultaneously presenting the virtual object at multiple views within a calibration interface (block 330). For example, the AR system 110 may simultaneously present the virtual object 102 at multiple views within a calibration interface, such as the calibration interface 100 of FIGS. 2A-2C. In some embodiments, the AR system 110 may simultaneously present the virtual object at multiple views through one or more viewers, such as AR reflective displays.

Process 300 also may include receiving user input aligning the virtual object with a real-world object at each of the presented views (block 340). For example, the AR system 110 may receive user input aligning the virtual object 102 with the real-world object 104 at each of the presented views (e.g., as described above with respect to FIGS. 2A-2C). In some embodiments, the AR system 110 may receive user input aligning the virtual object 102 with the real-world object 104 from the points of views of each calibration camera 120 (e.g., as shown through the viewers presenting the video captured by the calibration cameras 120). The AR system 110 may also receive user input aligning the virtual object 102 with the real-world object 104 at the user's viewing angle (e.g., from the user's point of view). In some embodiments, the virtual object 102 may record the user alignment input at each viewing angle/position in which the viewing position for each calibration camera 120 is obtained at block 310, and the viewing position from the user's point of view is obtained using any suitable geospatial recognition technique by the AR system 110 (e.g., gyroscopes, location determination devices, etc.).

In some embodiments, the user input may identify the locations on a coordinate plane in which the virtual object 102 is considered to be aligned (e.g., with respect to the real-world object 104) at these different angles. Additionally, or alternatively, the user input may identify offset measurements indicating an offset value or level for correcting a misalignment seen at various angles/points of views.

Process 300 further may include storing calibration definitions corresponding to the user alignment input (block 350). For example, the AR system 110 may store calibration definitions corresponding to the user alignment input (e.g., received at block 340). More specifically, the AR system 110 may store calibration definitions that identify the locations on the coordinate plane in which the virtual object 102 is considered to be aligned, as well as the viewing angle corresponding to these inputs (e.g., the viewing angle of the calibration cameras 120 and the viewing angle of the user when providing the alignment inputs). For example, the calibration definitions may identify the locations on a coordinate plane in which the virtual object 102 should be presented without misalignment based on the user's current viewing angle. In other words, the calibration definitions may identify the virtual object's correct or aligned position based on a current user viewing position or the user's current field of view.

In some embodiments, the calibration definitions identify an alignment offset to apply when rendering the virtual object 102 such that virtual object 102 is in proper alignment at various points of view. As described in greater detail herein, the stored calibration definitions may be used in a runtime operation to render the virtual object 102 with proper alignment based on the calibration definitions and the user's current viewing angle.

Figure 4:
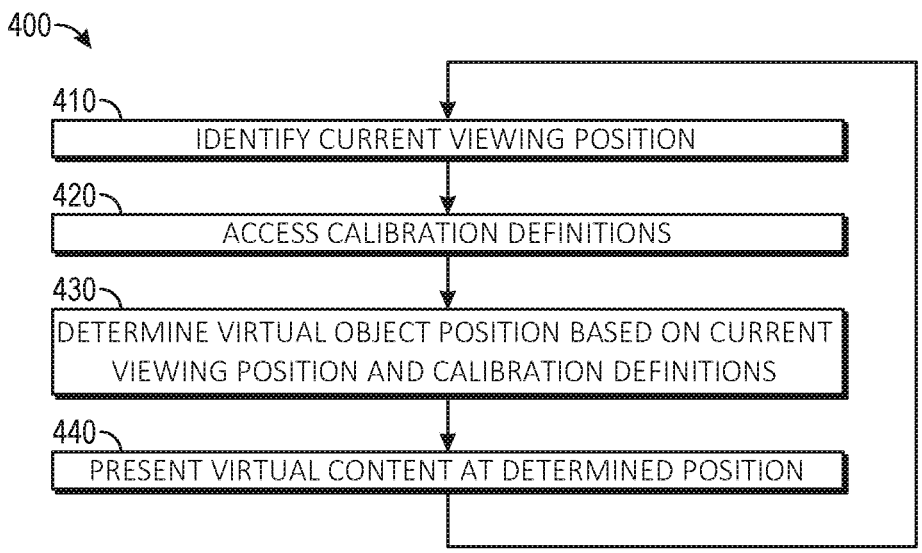
FIG. 4 illustrates an example flowchart of a process for rendering a virtual object at a proper alignment during a runtime operation using previously generated and stored calibration definitions.

FIG. 4 illustrates an example flowchart of a process 400 for rendering a virtual object at a proper alignment during a runtime operation using previously generated and stored calibration definitions. The flowchart of FIG. 4 illustrates the architecture, functionality, and operation of possible implementations of systems, methods, and computer program products according to various embodiments of the present disclosure. As described herein, the process 400 of FIG. 4 may be executed during runtime operations, such as an operation in which the virtual object 102 is to be presented within an AR system 110, and the virtual object 102 is to be used as a guide for positioning the real-world object 104. One illustrative, non-limiting example in which FIG. 4 may be performed is when using the AR system 110 in a surgical procedure to position the real-world object 104 (e.g., a real-world surgical arm) based on the projected image of the virtual object 102 (e.g., virtual surgical arm). More specifically, FIG. 4 may be implemented at a time when a user is using/wearing the AR system 110 and has instructed the AR system 110 to present the virtual object 102 for the purposes of aiding the user in positioning the real-world object 104.

As shown in FIG. 4, process 400 may include identifying a current viewing position (block 410). For example, the AR system 110 may identify the user's current viewing position using any suitable geospatial recognition technique by the AR system 110.

Process 400 also may include accessing calibration definitions (block 420). For example, the AR system 110 may access the calibration definitions previously generated and stored (e.g., in accordance with the process 300 of FIG. 3). As described herein, the calibration definitions identify the virtual object's correct or aligned position based on a current user viewing position.

Process 400 further may include determining the position of the virtual object based on the current viewing position and the calibration definitions (block 430). For example, the AR system 110 may determine the position that virtual object should be displayed (e.g., on a coordinate plane) based on the current viewing position (as identified at block 410) and the calibration definitions, which may identify the correct position of the virtual object based on the viewing position. Additionally, or alternatively, the AR system 110 may determine the offset for the virtual object based on the current viewing position and the calibration definitions.

Process 400 also may include presenting the virtual object at the determined position (block 440). For example, the AR system 110 may present the virtual object 102 at the determined position (e.g., determined at block 440). That is, the AR system 110 may present the virtual object at the correct location without misalignment, since the calibration definitions instruct the AR system 110 to render or adjust the rendering of the virtual object 102 based on the previous alignment inputs received at the calibration phase (e.g., as described at FIG. 3).

As further shown in FIG. 4, process 400 may be repeated such that as the user's viewing angle changes (e.g., as the user moves or adjusts their point of view), the presentation of the virtual object 102 is also updated based on the updated viewing angle and the calibration definitions identifying the correct position of the virtual object 102 based on current viewing angle. In this way, the user's viewing position/field of view is actively monitored, and the presentation of the virtual object will continuously update and remain in proper alignment as the user's current viewing position and field of view changes.

Figure 5:
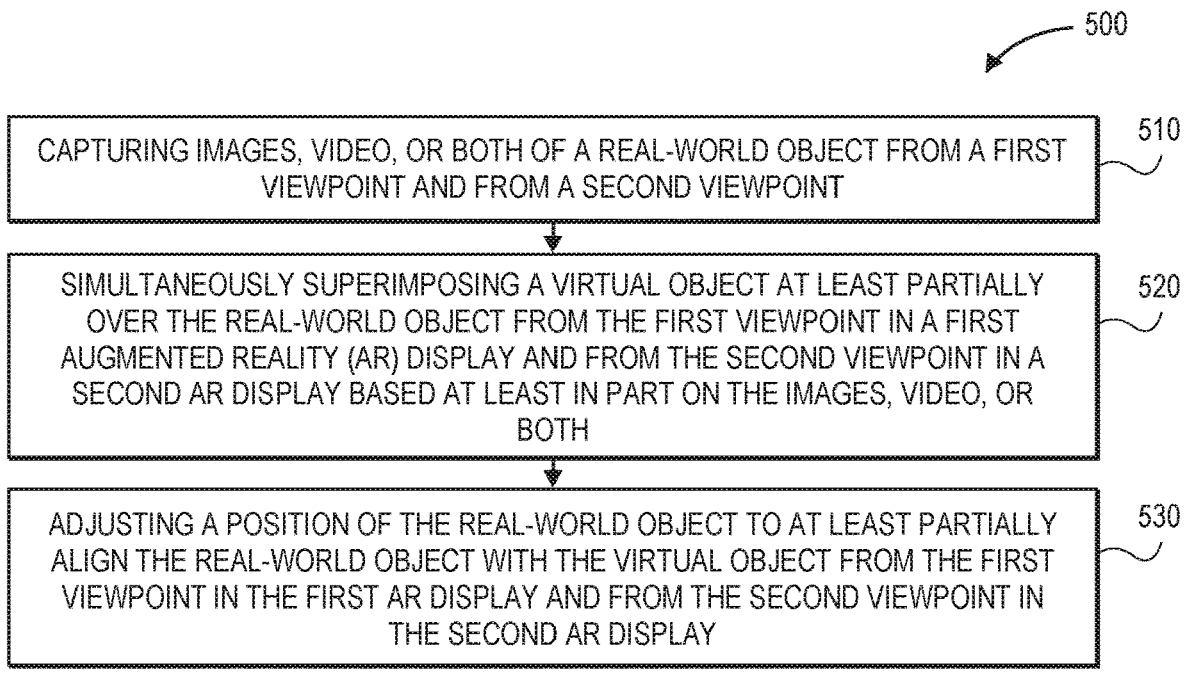
FIG. 5 illustrates an example of a flowchart for aligning a real-world object with a virtual object in accordance with aspects of the present disclosure.

FIG. 5 illustrates an example of a flowchart of a process 500 for aligning the real-world object 104 with the virtual object 102 in accordance with aspects of the present disclosure. An illustrative order of the process 500 is described below; however, one or more steps of the process 500 may be performed in a different order, performed simultaneously, repeated, or omitted.

Process 500 may include capturing images, video, or both of the real-world object 104 from a first viewpoint and from a second viewpoint (block 510). The images, video, or both may be captured by one or more cameras 120. In one example, a first set of images, video, or both may be captured from the first viewpoint by a first camera, and a second set of the images, video, or both may be captured from the second viewpoint by a second camera. The first and second sets may be captured simultaneously. In another example, the images, video, or both may be captured from the first viewpoint by a camera, and captured from the second viewpoint by the same camera (e.g., at a different time). The first and second viewpoints may be different.

Process 500 may also include (e.g., simultaneously) superimposing the virtual object 102 at least partially over the real-world object 104 from the first viewpoint in a first augmented reality (AR) display 202 and from the second viewpoint in a second AR display 204 based at least in part on the images, video, or both (block 520).

In at least one embodiment, the first and second AR displays 202, 204 may be (e.g., simultaneously) viewable through a head-mounted display (HMD). When two cameras are used, at least one camera may be mounted on the HMD, and at least one camera may not be mounted on the HMD.

The first AR display 202 may be or include a first reflective AR display that simulates a mirror-like view of the real-world object 104 and/or the virtual object 102 from the first viewpoint. The second AR display 204 may be or include a second reflective AR display that simulates a mirror-like view of the real-world object 104 and the virtual object 102 from the second viewpoint.

Process 500 may also include adjusting a position of the real-world object 104 to at least partially align the real-world object 104 with the virtual object 102 from the first viewpoint in the first AR display 202 and from the second viewpoint in the second AR display 204 (block 530).

In at least one embodiment, the real-world object 104 and the virtual object 102 may be substantially aligned in the first AR display 202 and not aligned in the second AR display 204. When this occurs, adjusting the position of the real-world object 104 substantially aligns the real-world object 104 with the virtual object 102 in both the first and second AR displays 202, 204.

The virtual object 102 that is superimposed at least partially over the real-world object 104 may be in a previously-saved position. Adjusting the position of the real-world object 104 at least partially aligns the real-world object 104 with the virtual object 102 in the previously-saved position.

The real-world object 104 may be or include a surgical device (e.g., a surgical arm and/or a surgical implant), and the virtual object 102 may be or include a virtual surgical device (e.g., a surgical arm and/or a surgical implant). Process 500 may also include performing a surgical procedure with the surgical device after the surgical device is at least partially aligned with the virtual surgical device.

Figure 6:
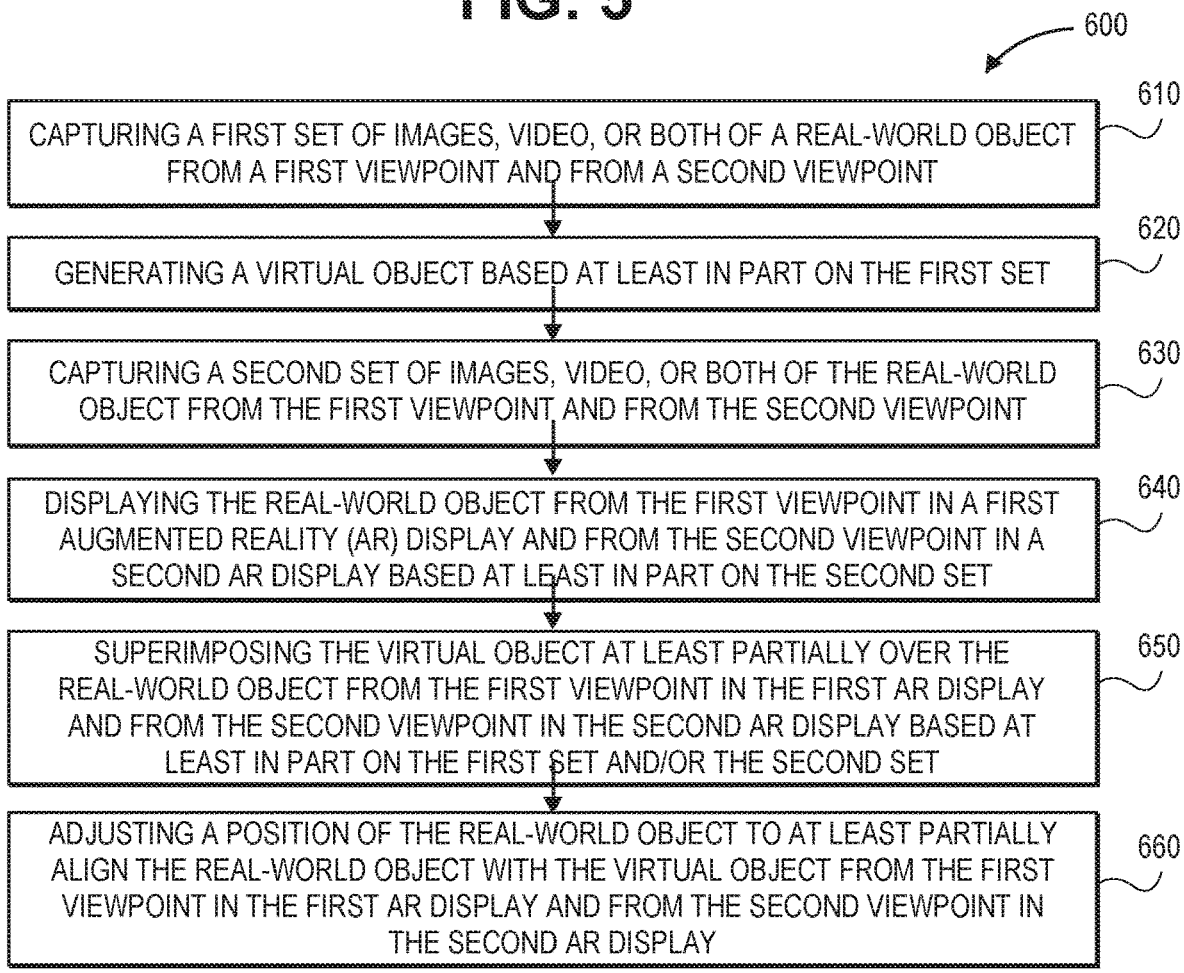
FIG. 6 illustrates another example of a flowchart for aligning a real-world object with a virtual object in accordance with aspects of the present disclosure.

FIG. 6 illustrates another example of a flowchart of a process 600 for aligning the real-world object 104 with the virtual object 102 in accordance with aspects of the present disclosure. An illustrative order of the process 600 is described below; however, one or more steps of the process 600 may be performed in a different order, performed simultaneously, repeated, or omitted.

Process 600 may include capturing a first set of images, video, or both of the real-world object 104 from a first viewpoint and from a second viewpoint (block 610). The first set may captured at a first time. The real-world object 104 may be in a predetermined position at the first time. The first and second viewpoints may be different.

Process 600 may also include generating the virtual object 102 based at least in part on the first set (block 620). Thus, the virtual object 102 may be in the predetermined position.

Process 600 may also include capturing a second set of images, video, or both of the real-world object 104 from the first viewpoint and from the second viewpoint at a second time (block 630). The second time is after the first time. In at least one embodiment, the second time may be real-time (or within about 5 seconds of real-time). In at least one embodiment, the real-world object 104 may not be in the predetermined position at the second time.

Process 600 may also include displaying the real-world object 104 from the first viewpoint in a first augmented reality (AR) display 202 and from the second viewpoint in a second AR display 204 based at least in part on the second set (block 640). Thus, the real-world object 104 may be displayed substantially in real-time (e.g., when the real-world object 104 is not in the predetermined position).

The first and second AR displays 202, 204 may be or include reflective AR displays that simulate mirror-like views of the real-world object 104 and the virtual object 102. In one embodiment, the first and second AR displays 202, 204 may not be in the same plane. In one embodiment, simulating the mirror-like views may include constructing a reversed frustum based at least in part on the first set, the second set, or both.

Process 600 may also include superimposing the virtual object 102 at least partially over the real-world object 104 from the first viewpoint in the first AR display 202 and from the second viewpoint in the second AR display 204 based at least in part on the first set and/or the second set (block 650). Thus, this may show the difference between the real-world object 104 (which may not be in the predetermined position) and the virtual object 102 (which may be in the predetermined position). The difference may be viewable in the first AR display 202, the second AR display 204, or both.

The real-world object 104 may be displayed, and the virtual object 102 may be superimposed, in the first and second AR displays 202, 204 simultaneously. The first and second AR displays 202, 204 may be viewable through the HMD.

Process 600 may also include adjusting a position of the real-world object 104 to at least partially align the real-world object 104 with the virtual object 102 from the first viewpoint in the first AR display 202 and from the second viewpoint in the second AR display 204 (block 660).

In at least one embodiment, the process 600 may be iterative such that movement of the real-world object 104, and the differences between the position of the real-world object 104 and the virtual object 102, may be viewable from the first viewpoint in the first AR display 202 and from the second viewpoint in the second AR display 204 substantially in real-time.

Figure 7:
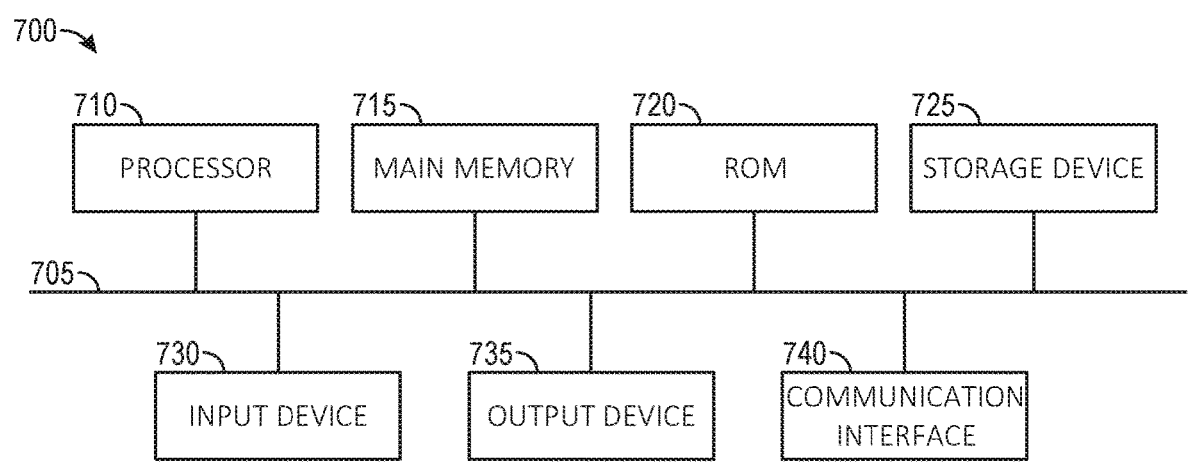
FIG. 7 illustrates example components of a device that may be used in connection with aspects of the present disclosure.

FIG. 7 illustrates example components of a device 700 that may be used in connection with aspects of the present disclosure. For example, device 700 may correspond to the AR system 110 and/or the calibration camera 120. Each of the AR system 110 and/or the calibration camera 120 may include one or more devices 700 and/or one or more components of device 700.

As shown in FIG. 7, device 700 may include a bus 705, a processor 710, a main memory 715, a read only memory (ROM) 720, a storage device 725, an input device 750, an output device 755, and a communication interface 740.

Bus 705 may include a path that permits communication among the components of device 700. Processor 710 may include a processor, a microprocessor, an application specific integrated circuit (ASIC), a field programmable gate array (FPGA), or another type of processor that interprets and executes instructions. Main memory 715 may include a random-access memory (RAM) or another type of dynamic storage device that stores information or instructions for execution by processor 710. ROM 720 may include a ROM device or another type of static storage device that stores static information or instructions for use by processor 710. Storage device 725 may include a magnetic storage medium, such as a hard disk drive, or a removable memory, such as a flash memory.

Input device 750 may include a component that permits an operator to input information to device 700, such as a control button, a keyboard, a keypad, or another type of input device. Output device 755 may include a component that outputs information to the operator, such as a light emitting diode (LED), a display, or another type of output device. Communication interface 740 may include any transceiver-like component that enables device 700 to communicate with other devices or networks. In some implementations, communication interface 740 may include a wireless interface, a wired interface, or a combination of a wireless interface and a wired interface. In embodiments, communication interface 740 may receiver computer readable program instructions from a network and may forward the computer readable program instructions for storage in a computer readable storage medium (e.g., storage device 725).

Device 700 may perform certain operations, as described in detail below. Device 700 may perform these operations in response to processor 710 executing software instructions contained in a computer-readable medium, such as main memory 715. A computer-readable medium may be defined as a non-transitory memory device and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. A memory device may include memory space within a single physical storage device or memory space spread across multiple physical storage devices.

The software instructions may be read into main memory 715 from another computer-readable medium, such as storage device 725, or from another device via communication interface 740. The software instructions contained in main memory 715 may direct processor 710 to perform processes that will be described in greater detail herein. Alternatively, hardwired circuitry may be used in place of or in combination with software instructions to implement processes described herein. Thus, implementations described herein are not limited to any specific combination of hardware circuitry and software.

In some implementations, device 700 may include additional components, fewer components, different components, or differently arranged components than are shown in FIG. 7.

In some embodiments, the devices used in connection with the techniques described herein may communicate via a network. In some embodiments, the network may include network nodes and one or more wired and/or wireless networks. For example, the network may include a cellular network (e.g., a second generation (2G) network, a third generation (3G) network, a fourth generation (4G) network, a fifth generation (2G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks. In embodiments, the network may include copper transmission cables, optical transmission fibers, wireless transmission, routers, firewalls, switches, gateway computers and/or edge servers.

The quantity of devices is not limited to what is shown in the above FIGS. That is, in practice, the devices may include additional components; fewer components, or differently arranged components that those illustrated in the FIGS. Also, in some implementations, one or more of the illustrated devices may perform one or more functions described as being performed by another one or more of the devices. The devices shown in the FIGS. may interconnect via wired connections, wireless connections, or a combination of wired and wireless connections.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may include a system, a method, and/or a computer program product at any possible technical detail level of integration. The computer program product may include a computer readable storage medium (or media) having computer readable program instructions thereon for causing a processor to carry out or execute aspects and/or processes of the present disclosure.

In embodiments, the computer readable program instructions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on a user's computer, partly on the user's computer, as a stand-alone software package, partly on the user's computer and partly on a remote computer or entirely on the remote computer or server.

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In embodiments, a service provider could offer to perform the processes described herein. In this case, the service provider can create, maintain, deploy, support, etc., the computer infrastructure that performs the process steps of the disclosure for one or more customers. These customers may be, for example, any business that uses technology. In return, the service provider can receive payment from the customer(s) under a subscription and/or fee agreement and/or the service provider can receive payment from the sale of advertising content to one or more third parties.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While the present disclosure has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the disclosure.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A method for aligning a real-world object with a virtual object, the method comprising:
   capturing images, video, or both of the real-world object from a first viewpoint and from a second viewpoint, wherein the first and second viewpoints are different;
   simultaneously superimposing the virtual object at least partially over the real-world object from the first viewpoint in a first augmented reality (AR) display and from the second viewpoint in a second AR display based at least in part on the images, video, or both, wherein the real-world object and the virtual object are substantially aligned in the first AR display and not aligned in the second AR display; and
   adjusting a position of the real-world object to at least partially align the real-world object with the virtual object from the first viewpoint in the first AR display and from the second viewpoint in the second AR display.

2. The method of claim 1, wherein the first and second AR displays are simultaneously viewable through a head-mounted display (HMD).

3. The method of claim 2, wherein the images, video, or both of the real-world object are captured simultaneously from the first viewpoint by a first camera and from the second viewpoint by a second camera.

4. The method of claim 3, wherein the first camera is mounted on the HMD, and wherein the second camera is not mounted on the HMD.

5. The method of claim 1, wherein the images, video, or both of the real-world object are captured from the first viewpoint and the second viewpoint by a single camera that is moved to two different locations.

6. The method of claim 1, wherein the virtual object that is superimposed at least partially over the real-world object is in a previously-saved position, and wherein adjusting the position of the real-world object at least partially aligns the real-world object with the virtual object in the previously-saved position.

7. The method of claim 1, wherein the first AR display comprises a first reflective AR display that simulates a mirror-like view of the real-world object and the virtual object from the first viewpoint.

8. The method of claim 7, wherein the second AR display comprises a second reflective AR display that simulates a mirror-like view of the real-world object and the virtual object from the second viewpoint.

9. The method of claim 1, wherein the real-world object comprises a surgical device, wherein the virtual object comprises a virtual surgical device and wherein the method further comprises performing a surgical procedure with the surgical device after the surgical device is at least partially aligned with the virtual surgical device.

10. A method for aligning a real-world object with a virtual object, the method comprising:
    capturing a first set of images, video, or both of the real-world object from a first viewpoint and from a second viewpoint, wherein the first set is captured at a first time, and wherein the first and second viewpoints are different;
    generating the virtual object based at least in part on the first set;
    capturing a second set of images, video, or both of the real-world object from the first viewpoint and from the second viewpoint, wherein the second set is captured at a second time, and wherein the second time is after the first time;
    displaying the real-world object from the first viewpoint in a first augmented reality (AR) display and from the second viewpoint in a second AR display based at least in part on the second set;
    superimposing the virtual object at least partially over the real-world object from the first viewpoint in the first AR display and from the second viewpoint in the second AR display based at least in part on the first set and the second set, wherein the real-world object and the virtual object are substantially aligned in the first AR display and not aligned in the second AR display; and
    adjusting a position of the real-world object to at least partially align the real-world object with the virtual object from the first viewpoint in the first AR display and from the second viewpoint in the second AR display.

11. The method of claim 10, wherein the real-world object is displayed, and the virtual object is superimposed, in the first and second AR displays simultaneously.

12. The method of claim 11, wherein the first and second AR displays are viewable through a head-mounted display (HMD).

13. The method of claim 12, wherein the first and second AR displays comprise reflective AR displays that simulate mirror-like views of the real-world object and the virtual object, and wherein the first and second AR displays are not in the same plane.

14. The method of claim 13, wherein simulating the mirror-like views comprises constructing a reversed frustum based at least in part on the first set, the second set, or both.

15. A system for aligning a real-world object with a virtual object, the system comprising:
- a first camera configured to capture a first set of images, video, or both of the real-world object at a first time and a second set of images, video, or both of the real-world object at a second time, wherein the first time is before the second time, and wherein the first and second sets are from a first viewpoint;
- a second camera configured to capture a third set of images, video, or both of the real-world object at the first time and a fourth set of images, video, or both of the real-world object at the second time, wherein the third and fourth sets are from a second viewpoint, and wherein the first and second viewpoints are different;
- a viewing device configured to:
  - display the virtual object from the first viewpoint in a first augmented reality (AR) display and from the second viewpoint in a second AR display based at least in part on the first set and the third set; and
  - display the real-world object from the first viewpoint in the first AR display and from the second viewpoint in the second AR display based at least in part on the second set and the fourth set, wherein the real-world object and the virtual object are substantially aligned in the first AR display and not aligned in the second AR display; and
- a computing system configured to receive a user input in response to the virtual object and the real-world object in the first and second AR displays and to adjust a position of the real-world object to at least partially align the real-world object with the virtual object from the first viewpoint in the first AR display and from the second viewpoint in the second AR display.

16. The system of claim 15, wherein the virtual object is at least partially superimposed over the real-world object in the first and second AR displays.

17. The system of claim 15, wherein the viewing device comprises a head-mounted display (HMD) that is configured to simultaneously display the virtual object and the real-world object from the first viewpoint tin the first AR display and from the second viewpoint in the second AR display.

18. The system of claim 15, wherein the real-world object comprises a surgical arm, wherein the virtual object comprises a virtual surgical arm.

19. The system of claim 15, wherein the first and second viewpoints are oriented at an angle with respect to one another, and wherein the first and second AR displays are oriented at the angle with respect to one another.

* * * * *